（12）United States Patent
Maruyama

(10) Patent No.: US 10,143,586 B2
(45) Date of Patent: Dec. 4, 2018

(54) TREATMENT METHOD AND STENT

(71) Applicant: Terumo Kabushiki Kaisha, Shibuya-ku, Tokyo (JP)

(72) Inventor: Naoko Maruyama, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 3 days.

(21) Appl. No.: 15/423,930

(22) Filed: Feb. 3, 2017

(65) Prior Publication Data

US 2017/0224535 A1 Aug. 10, 2017

(30) Foreign Application Priority Data

Feb. 8, 2016 (JP) .................................. 2016-022262

(51) Int. Cl.
*A61F 9/007* (2006.01)
*A61F 2/82* (2013.01)
*A61F 9/00* (2006.01)
*A61F 2/962* (2013.01)

(52) U.S. Cl.
CPC ............ *A61F 9/00727* (2013.01); *A61F 2/82* (2013.01); *A61F 9/0017* (2013.01); *A61F 9/00781* (2013.01); *A61F 2/962* (2013.01); *A61F 2210/0004* (2013.01); *A61F 2250/0091* (2013.01)

(58) Field of Classification Search
CPC .... A61F 9/00727; A61F 9/00736; A61F 2/14; A61F 2/962; A61F 2250/0091; A61F 2210/0004
See application file for complete search history.

(56) References Cited

U.S. PATENT DOCUMENTS

| 5,846,258 A | 12/1998 | Takayanagi et al. |
| 6,019,778 A * | 2/2000 | Wilson ...................... A61F 2/95 606/198 |
| 2005/0228402 A1* | 10/2005 | Hofmann ............... A61B 17/22 606/108 |
| 2013/0046382 A1* | 2/2013 | Mazzocchi ........... A61F 9/0017 623/6.63 |

FOREIGN PATENT DOCUMENTS

JP H10-179629 7/1998

* cited by examiner

*Primary Examiner* — Howie Matthews
(74) *Attorney, Agent, or Firm* — Sheridan Ross. P.C.

(57) ABSTRACT

A treatment method is provided that includes an introduction step of introducing a transparent stent into a vitreous body of an eyeball, an expansion step of causing the stent to expansively deform inside the vitreous body to bring a retina into contact with a retinal pigment epithelium, and a placement step of placing the stent in the vitreous body with the stent keeping the retina in contact with the retinal pigment epithelium.

20 Claims, 8 Drawing Sheets

TREATMENT METHOD AND STENT

CROSS REFERENCE To RELATED APPLICATIONS

The present application claims the benefit of priority, under 35 U.S.C. § 119(e), to Japanese Application No. 2016-022262, filed Feb. 8, 2016, entitled "Method of Treatment, and the Stent," the entire disclosure of which is incorporated herein by reference in its entirety, for all that it teaches and for all purposes.

TECHNICAL FIELD

The present invention relates to a treatment method for retinal detachment and a stent used in the treatment of retinal detachment.

BACKGROUND

Retinal detachment is a disorder of the eyeball in which the retina separates from the retinal pigment epithelium, and, without treatment thereof, may cause vision loss. In particular, recently, with an increase in diabetes mellitus, diabetic retinopathy, which occurs in conjunction with diabetes mellitus, has been increasing. Diabetic retinopathy is the number one reason for blindness in Japan, and causes blindness to about three thousand or more persons per year. With respect to such retinal detachment, various treatment methods have been proposed.

For example, a method for treating retinal detachment by inserting a balloon into the eye and injecting a gas into the balloon to return the retina to its normal site is discussed in Japanese Patent Application No. JP-A-10-179629, which is incorporated by reference herein for all that it teaches and for all purposes, set forth below. According to this method, retinal detachment can be treated by keeping the balloon inflated for a predetermined period of time until the retina is tightly fixed to the retinal pigment epithelium.

SUMMARY

Problems Solved

However, in the above-mentioned method, since the balloon presses the entire inner peripheral surface of the retina for a predetermined period of time until the retina is tightly fixed to the retinal pigment epithelium, the intraocular pressure of a patient may increase during treatment, thus causing the occurrence of, for example, headache or glaucoma.

Therefore, an objective of the embodiments herein is to provide a treatment method and a stent capable of treating retinal detachment while preventing an increase in intraocular pressure.

Means for Solving the Problem(s)

A treatment method includes an introduction step of introducing a transparent stent into a vitreous body of an eyeball, an expansion step of causing the stent to expansively deform inside the vitreous body to bring a retina into contact with a retinal pigment epithelium, and a placement step of placing the stent in the vitreous body with the stent keeping the retina in contact with the retinal pigment epithelium.

Furthermore, a stent has transparency and is configured to be placed in a vitreous body of an eyeball in a state of expansively deforming the inside the vitreous body to keep a retina in contact with a retinal pigment epithelium.

Advantages

According to the treatment method and the stent, the stent is placed in the vitreous body while the stent keeps the retina in contact with the retinal pigment epithelium. Here, since the stent is composed of a plurality of linear objects, the stent is able to bring the retina into contact with the retinal pigment epithelium with a contact area with the inner peripheral surface of the retina reduced as compared with a balloon that presses the entire inner peripheral surface of the retina during treatment, thus tightly fixing the retina to the retinal pigment epithelium. Accordingly, retinal detachment can be treated with an increase in intraocular pressure prevented. Furthermore, since the stent has transparency, the stent is unlikely to hinder vision even in the state of being placed in the vitreous body.

DETAILED DESCRIPTION

Figure 1:
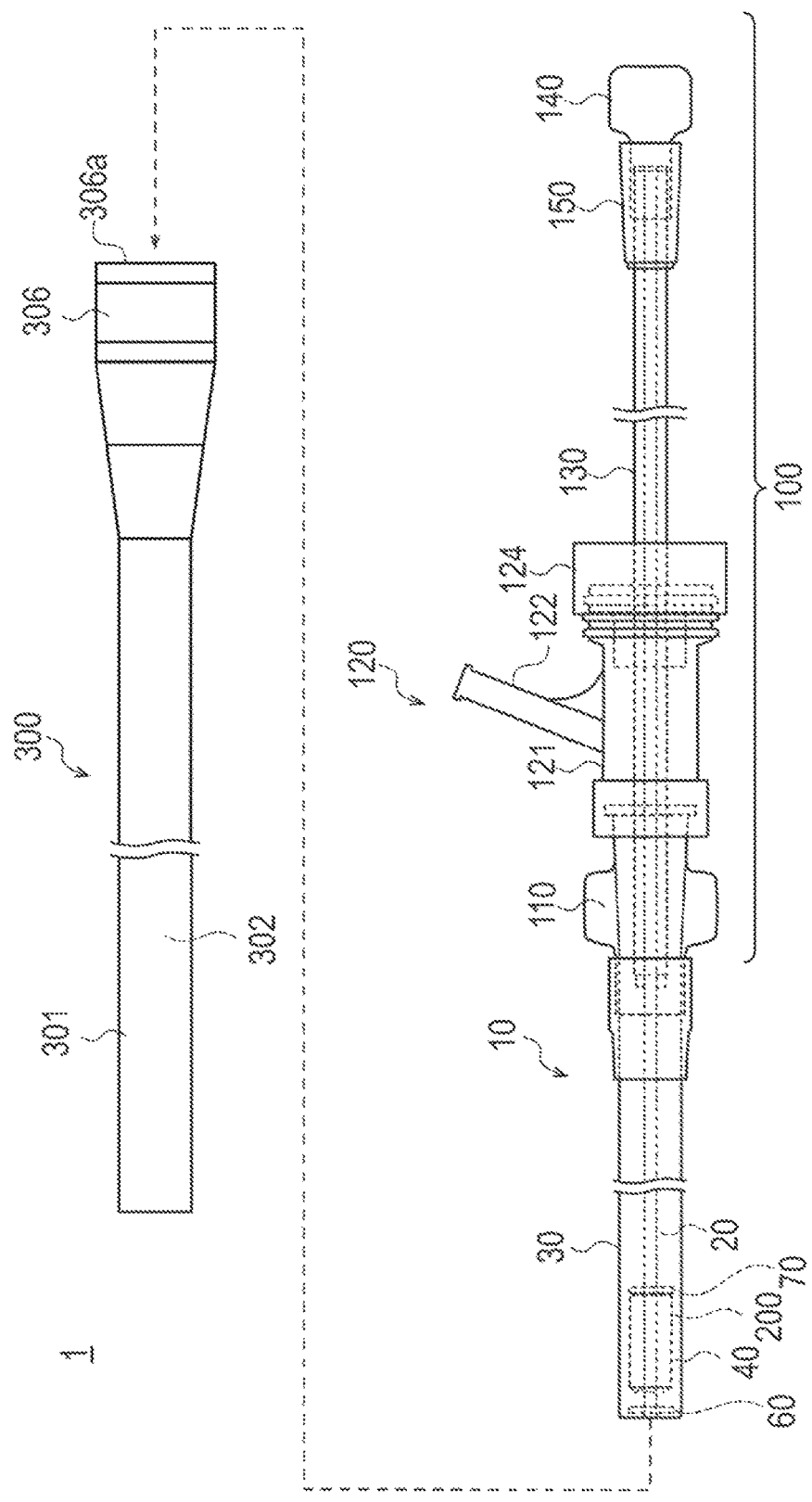
FIG. 1 is an overall configuration diagram of a treatment device for retinal detachment.

Hereinafter, embodiments herein will be described with reference to the accompanying drawings. Moreover, dimensional ratios illustrated in the drawings are exaggerated for the purpose of illustration and may be different from the actual ratios.

Figure 2:
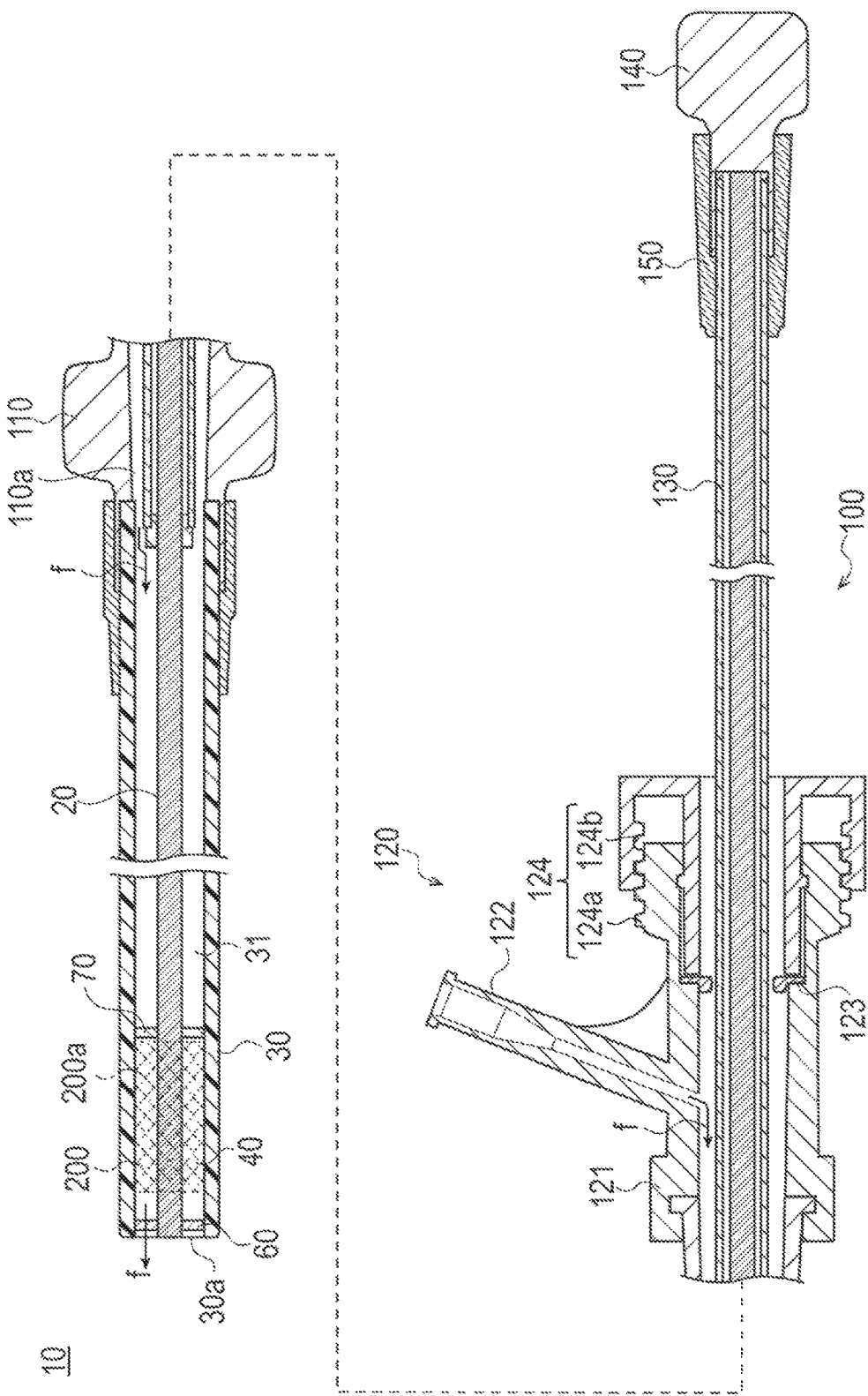
FIG. 2 is a cross-sectional view taken along the longitudinal direction of a stent delivery system.
Figure 3:
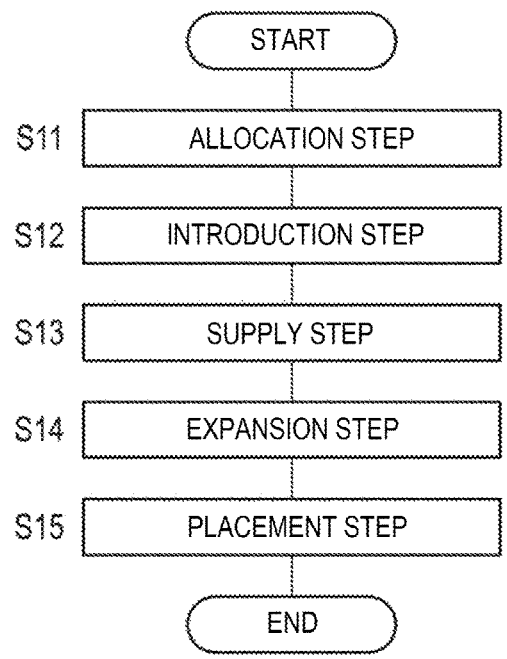
FIG. 3 is a flowchart illustrating steps of a treatment method for retinal detachment.

FIG. 1 and FIG. 2 are diagrams illustrating configurations of various portions of a treatment device 1 for retinal detachment (hereinafter referred to simply as a "treatment device 1"); FIG. 3 is a flowchart illustrating steps of a treatment method for retinal detachment. FIG. 4 to FIG. 8 are diagrams schematically illustrating the respective steps of the treatment method for retinal detachment.

First, a configuration of the treatment device 1, which is appropriately applied to the treatment method for retinal detachment, is described.

As illustrated in FIG. 1, the treatment device 1 includes a catheter 300 and a stent delivery system 10. Moreover, the side with which the introduction into an eyeball is performed is referred to as a "distal side", the side which is opposite to the distal side is referred to as a "proximal side", and the direction along which each of the catheter 300 and the stent delivery system 10 extends is referred to as an "axial direction".

A configuration of the catheter 300 is described.

As illustrated in FIG. 1, the catheter 300 includes a shaft 301 extending in the axial direction and a hub 306 provided at the proximal side of the shaft 301.

A delivery lumen 302 extending in the axial direction is formed inside the catheter 300. The delivery lumen 302 constitutes a delivery route used to deliver a stent 200 to inside a vitreous body when the catheter 300 is introduced into the vitreous body, as described below (refer to FIG. 4).

A predetermined port 306a is provided at the proximal end of the hub 306.

The material used to form the catheter 300 is not limited as long as it is unlikely to readily break, has an appropriate hardness that does not damage tissues within the eyeball, and is safe, and can be, for example, polypropylene or polymethylmethacrylate.

A configuration of the stent delivery system 10 is described.

As illustrated in FIG. 1 and FIG. 2, the stent delivery system 10 includes an inner tube 20 formed to extend in the axial direction, an outer tube 30 arranged in such a way as to cover the distal portion side of the inner tube 20, a stent 200 arranged between the distal portion of the inner tube 20 and the distal portion of the outer tube 30 and configured to expansively deform by being discharged from between the inner tube 20 and the outer tube 30 along with movement of the outer tube 30, and a hand operation portion 100 arranged at the proximal side of the inner tube 20 and configured to be gripped by a human hand.

As illustrated in FIG. 2, the inner tube 20 is formed of an elongated tube shaped body extending in the axial direction. Moreover, the inner tube 20 has a solid shape.

The material used to form the inner tube 20 is desirably a material having flexibility, and can be, for example, polyolefin such as polyethylene or polypropylene, polyester such as polyamide or polyethylene terephthalate, fluorine-based polymer such as ETFE, PEEK, or polyimide.

The inner tube 20 can be formed with an outer diameter of, for example, 1.0 mm to 1.5 mm inclusive.

As illustrated in FIG. 2, the outer tube 30 is formed of an elongated tube shaped body, and is equipped with an accommodation lumen 31, in which the inner tube 20 and the stent 200 or the like are accommodated. Furthermore, the outer tube 30 is arranged at the outer surface side of the inner tube 20 in such a way as to be relatively movable with respect to the inner tube 20.

A gap portion 40, which is provided to accommodate the stent 200, is formed between the distal portion of the inner tube 20 and the distal portion of the outer tube 30.

The gap portion 40 is formed of a space partitioned between a distal end marker 60 and a stent stopper 70, which are arranged inside the outer tube 30, and the inner wall of the outer tube 30. The stent 200, in the stage of not yet being placed in the vitreous body, is accommodated in the gap portion 40 while being compressed in the radially inward direction (refer to FIG. 5).

The material used to form the outer tube 30 can be the same as the material used to form the inner tube 20.

The outer tube 30 can be formed with an outer diameter of, for example, 2.0 mm to 2.5 mm inclusive.

As illustrated in FIG. 2, the distal end marker 60, which is arranged inside the outer tube 30, is fixed to the outer surface of the inner tube 20. Since the outer diameter of the distal end marker 60 is formed substantially equal to the inner diameter of the outer tube 30, frictional force acts between the outer surface of the inner tube 20 and the inner surface of the outer tube 30 via the distal end marker 60. The acting frictional force prevents the outer tube 30 from unexpectedly moving with respect to the inner tube 20. Furthermore, the distal end marker 60 can be formed of a material having radiopacity. The distal end marker 60 is provided partially in the circumferential direction.

The stent stopper 70 is arranged nearer the proximal side than the stent 200 accommodated in the gap portion 40. When an operation is performed to move the outer tube 30 toward the proximal side with respect to the inner tube 20, the proximal end of the stent 200 comes into contact with the stent stopper 70. The stent 200 is restricted by such contact from moving toward the proximal side. Since the outer tube 30 further moves toward the proximal side independent from the stent 200, the stent 200 with the proximal end thereof supported by the stent stopper 70 is extruded from between the inner tube 20 and the outer tube 30 and is then released to inside the vitreous body (refer to FIG. 7). The stent stopper 70 is provided partially in the circumferential direction. Moreover, the distal end marker 60 and the stent stopper 70 do not need to be provided.

The stent 200, in the state of being accommodated in the gap portion 40, receives constraint force from the inner surface of the outer tube 30, and is thus restricted from expansively deforming in the radially outward direction.

Figure 7:
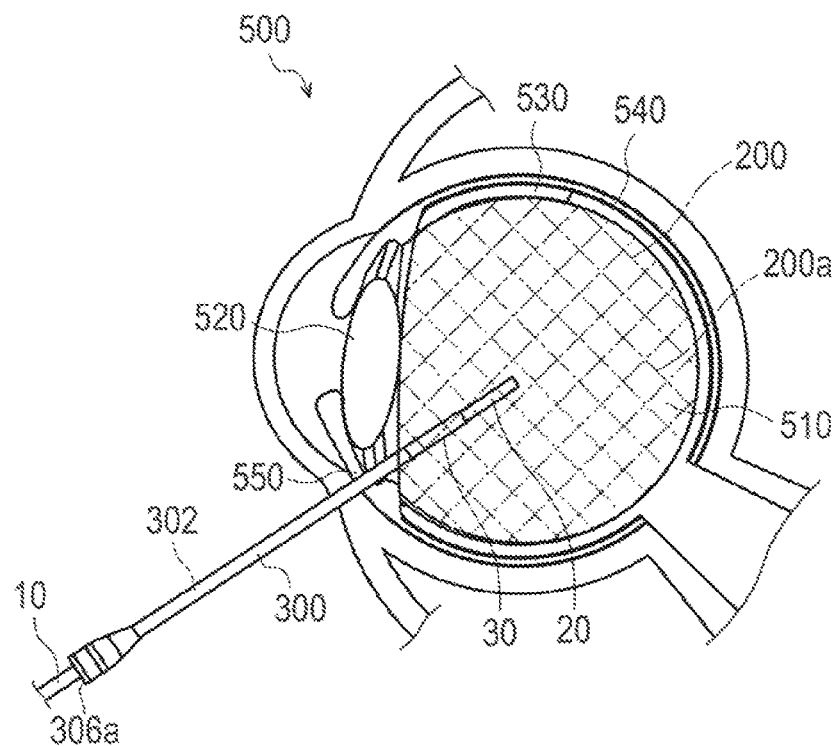
FIG. 7 is a diagram schematically illustrating an expansion step in the treatment method for retinal detachment.

When the outer tube 30 moves toward the proximal side with respect to the inner tube 20 and the gap portion 40 becomes exposed to the outside, the stent 200 is released from the constraint imposed by the inner surface of the outer tube 30 and, thus, expansively deforms in the radially outward direction into an approximately spherical shape matched with the shape of the vitreous body (refer to FIG. 7). As illustrated in FIG. 2, the stent 200 is formed in a mesh-like shape with a plurality of linear objects 200a aggregated.

The stent 200 can be formed, for example, with an outer diameter in an expanded state of 20 mm to 25 mm inclusive.

The stent 200 to be used can be, as appropriate, a known stent having transparency, self-expandability, and biodegradability. Such a stent 200 can be formed of, for example, a high-polymer material. Examples of the high-polymer material include polyolefin such as polyethylene or polypropylene, polyester such as polyethylene terephthalate, and fluorine-containing polymer such as polytetrafluoroethylene or tetrafluoroethylene-ethylene copolymer.

As illustrated in FIG. 1 and FIG. 2, the hand operation portion 100 includes an outer tube hub 110, to which the proximal portion of the outer tube 30 is attached, a connector (Y connector) 120, which is connected to the proximal end of the outer tube hub 110 and is provided to be movable together with the outer tube 30, a proximal portion shaft 130, which covers the inner tube 20 at the proximal side of the connector 120, and an inner tube hub 140, to which the proximal end of the inner tube 20 is attached.

As illustrated in FIG. 2, the outer tube hub 110 is connected to the proximal portion of the outer tube 30 in a liquid-tight manner. A lumen 110a of the outer tube hub 110 communicates with the accommodation lumen 31 of the outer tube 30. The outer tube hub 110 can be formed of, for example, a known resin material or metallic material.

The connector 120 is detachably connected to the outer tube hub 110. The connector 120 includes a main body portion 121, which communicates with the accommodation lumen 31 of the outer tube 30 and into which the inner tube 20 is inserted through, a branch tube 122, which branches from the main body portion 121, a valve body 123, which is arranged to freely open and close a lumen of the main body portion 121, and a cap body 124, which is provided at the proximal side of the main body portion 121.

The main body portion 121 is provided to be relatively movable with respect to the inner tube 20, and moving the main body portion 121 toward the proximal side with respect to the inner tube 20 enables moving the outer tube 30 toward the proximal side with respect to the inner tube 20. This operation enables the stent 200 to expansively deform.

A known fluid supply source (not illustrated), such as a prefilled syringe filled with, for example, a medicine f that promotes tight fixing of the retina to the retinal pigment epithelium, is connected to the branch tube 122 via a predetermined fluid tube. When the medicine f is supplied while the stent delivery system 10 is inserted in the vitreous body, the medicine f is discharged from a gap 30a between the outer tube 30 and the inner tube 20 at the distal side via the branch tube 122, the accommodation lumen 31 of the outer tube 30, the stent stopper 70 partially provided in the circumferential direction, and the distal end marker 60, as indicated by arrows illustrated in FIG. 2, so that the medicine f can be supplied to between the retina and the retinal pigment epithelium (refer to FIG. 6). As a result of this configuration, tight fixing of the retina to the retinal pigment epithelium is promoted.

As illustrated in FIG. 2, the valve body 123 is arranged to surround the outer periphery of the proximal portion shaft 130 in the lumen of the main body portion 121 and is provided to freely open and close the gap between the main body portion 121 and the proximal portion shaft 130. The opening or closing operation on the valve body 123 is performed using the cap body 124 described below.

The material used to form the valve body 123 is not specifically limited as long as it is a material having flexibility and liquid-tightness, and can be, for example, a known elastic material, such as natural rubber, synthetic rubber, and various thermoplastic elastomers, such as polyamide system and polyester system. Among others, silicone rubber, which is superior in restorability for compression and deformation in a wide temperature range, can be appropriately used.

When the valve body 123 is in an open state, the connector 120 is relatively movable with respect to the proximal portion shaft 130. This configuration enables moving the outer tube 30 relatively with respect to the inner tube 20.

When the valve body 123 is in a fully closed state, since the outer periphery of the proximal portion shaft 130 is brought into press contact with (clamped by) the valve body 123, the lumen of the main body portion 121 is kept in a liquid-tight state at the distal side of the valve body 123, and the relative movement of the outer tube 30 with respect to the inner tube 20 is restricted. This configuration enables preventing the above-mentioned medicine f from leaking when the medicine f is supplied to the main body portion 121 and the accommodation lumen 31 of the outer tube 30 via the branch tube 122. Furthermore, since, when the stent delivery system 10 is introduced into the vitreous body, the relative position between the outer tube 30 and the inner tube 20 does not vary, operability can be improved.

The cap body 124 includes a female thread portion 124b, which is screwed with a male thread portion 124a, which is formed on the outer surface of the proximal portion of the main body portion 121. When the female thread portion 124b is rotated with respect to the male thread portion 124a, with these thread portions screwed with each other, the valve body 123 is driven to open and close in the radially inward direction.

The material used to form each of the main body portion 121, the branch tube 122, and the cap body 124 is not specifically limited, and can be, for example, polyvinyl chloride, polyethylene, polypropylene, cyclic polyolefin, polystyrene, poly(4-methyl pentene-1), polycarbonate, acrylic resin, acrylonitrile-butadiene-styrene copolymer, polyester, such as polyethylene terephthalate and polyethylene naphthalate, butadiene-styrene copolymer, or polyamide (for example, nylon 6, nylon 6,6, nylon 6,10, and nylon 12).

The proximal portion shaft 130 has a hollow pipe shape into which the inner tube 20 is able to be inserted through. The proximal portion shaft 130 can be made from, for example, stainless steel or nitinol.

As illustrated in FIG. 2, the proximal end of the proximal portion shaft 130 is fixed to the inner tube hub 140 included in the hand operation portion 100. The inner tube 20 is inserted through into the inner tube hub 140 together with the proximal portion shaft 130.

The inner tube hub 140 is connected to the proximal portion shaft 130 and the proximal portion of the inner tube 20.

The material used to form the inner tube hub 140 includes, for example, thermoplastic resin, such as polycarbonate, polyamide, polysulfone, polyarylate, and methacrylate-styrene copolymer.

A grip portion 150 is provided on the outer periphery of a portion at which the proximal portion shaft 130 and the inner tube hub 140 are connected to each other. The grip portion 150 is a portion which the operator grips when operating the hand operation portion 100, and, for example, knurling for preventing slip can be applied to the outer periphery thereof.

Next, the treatment method for retinal detachment is described with reference to FIG. 3 to FIG. 8. Moreover, FIG. 4 to FIG. 6 illustrate a condition indicating symptoms of retinal detachment in which the retina 530 separates from the retinal pigment epithelium 540 and a retinal tear 531 occurs due to a break in the retina 530.

As illustrated in FIG. 3, the treatment method for retinal detachment, broadly described, includes an allocation step S11, an introduction step S12, a supply step S13, an expansion step S14, and a placement step S15. Hereinafter, the respective steps are described in order.

Figure 4:
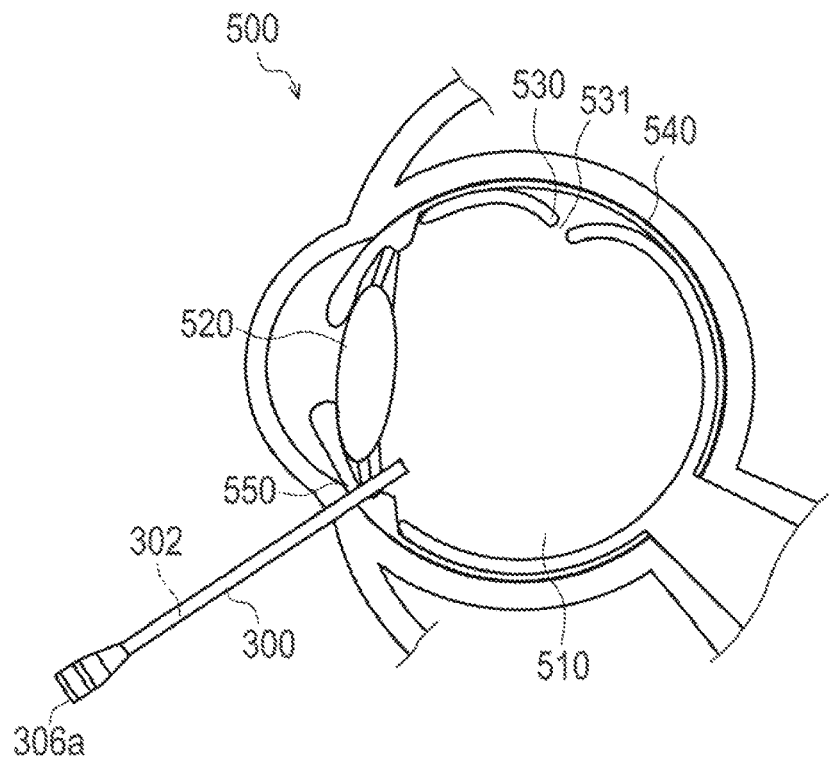
FIG. 4 is a diagram schematically illustrating an allocation step in the treatment method for retinal detachment.

First, as illustrated in FIG. 4, the operator performs an operation for inserting the catheter 300 into the vitreous body 510 of the eyeball 500 and allocating a delivery route leading to inside the vitreous body 510 (allocation step S11). More specifically, the operator uses a treatment tool (not illustrated) to make an incision with a predetermined size in the pars plana 550, which is provided underneath the crystalline lens 520. Next, the operator inserts the catheter 300 into the vitreous body 510 through the incised portion. As a result of this insertion, the delivery lumen 302 of the catheter 300 constitutes a delivery route leading to inside the vitreous body 510.

Figure 5:
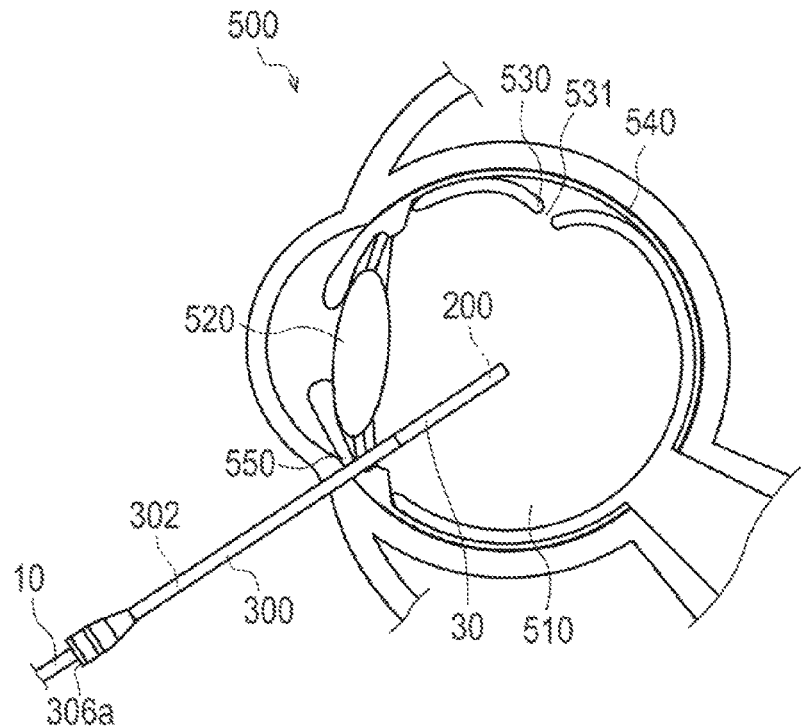
FIG. 5 is a diagram schematically illustrating an introduction step in the treatment method for retinal detachment.
Figure 6:
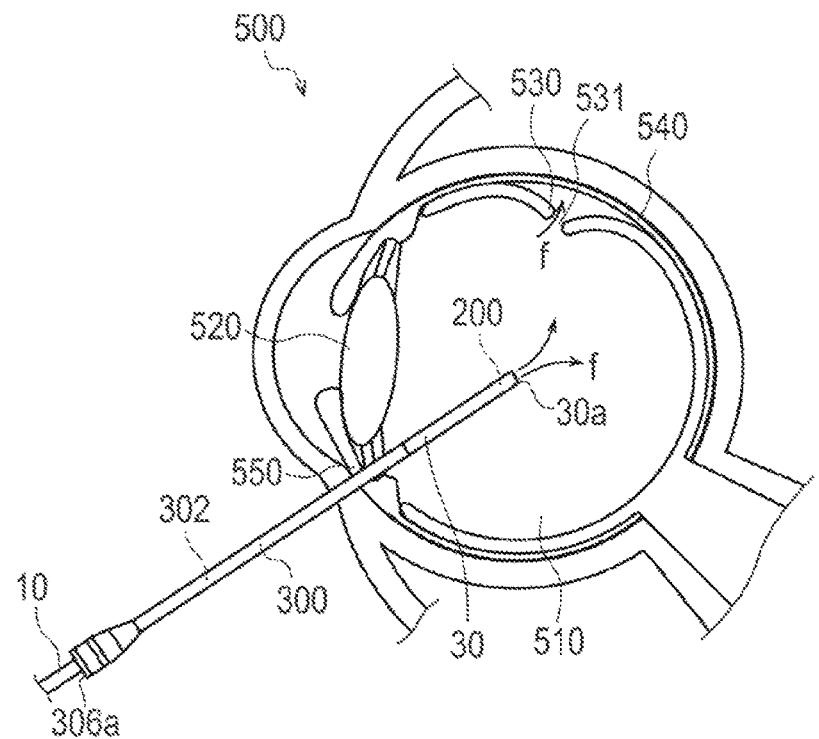
FIG. 6 is a diagram schematically illustrating a supply step in the treatment method for retinal detachment.

Next, as illustrated in FIG. 5, the operator performs an operation for introducing the transparent stent 200 into the vitreous body 510 of the eyeball 500 (introduction step S12).

More specifically, the operator inserts the stent delivery system 10 through the port 306a of the catheter 300 and introduces the stent delivery system 10 into the vitreous body 510 via the delivery lumen 302, which is a delivery route allocated in the allocation step S11. According to this operation, the stent 200, which is arranged at the distal side of the stent delivery system 10, is introduced into the vitreous body 510.

Next, as illustrated in FIG. 6, the operator supplies the medicine f to between the retina 530 and the retinal pigment epithelium 540 (supply step S13). More specifically, the operator connects the fluid supply source filled with the medicine f to the branch tube 122. Then, the operator discharges the medicine f from the gap 30a between the outer tube 30 and the inner tube 20 at the distal side via the accommodation lumen 31, the stent stopper 70, and the distal end marker 60 of the outer tube 30. In this way, when the medicine f is supplied to inside the vitreous body 510, the medicine f is supplied to between the retina 530 and the retinal pigment epithelium 540 via the retinal tear 531 and then osmoses into the boundary surface between the retina 530 and the retinal pigment epithelium 540, so that tight fixing of the retina 530 to the retinal pigment epithelium 540 is promoted in the placement step S15 described below.

Next, as illustrated in FIG. 7, the operator causes the stent 200 to expansively deform inside the vitreous body 510 to bring the retina 530 into contact with the retinal pigment epithelium 540 (expansion step S14). More specifically, the operator moves the outer tube 30 toward the proximal side with respect to the inner tube 20 (refer to FIG. 2). With this, the gap portion 40 becomes exposed to the outside, and the stent 200, which is of a self-expandable type, is discharged from between the inner tube 20 and the outer tube 30 and then expansively deforms. Then, the stent 200, which has expansively deformed inside the vitreous body 510, brings the retina 530 into contact with the retinal pigment epithelium 540.

Figure 8:
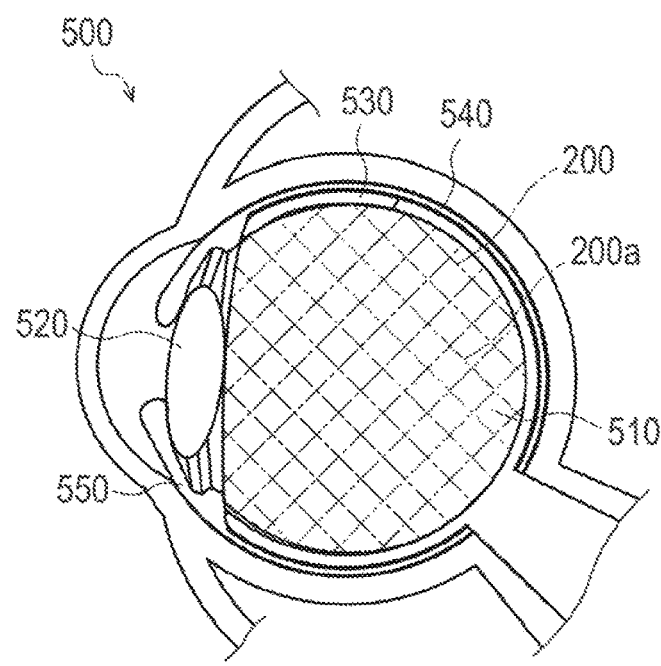
FIG. 8 is a diagram schematically illustrating a placement step in the treatment method for retinal detachment.

Next, as illustrated in FIG. 8, the operator places the stent 200 in the vitreous body 510 with the stent 200 keeping the retina 530 in contact with the retinal pigment epithelium 540 (placement step S15). More specifically, the operator extracts the catheter 300, the inner tube 20, and the outer tube 30 to place the stent 200 in the vitreous body 510.

Then, after a predetermined period of time elapses and the retina 530 is tightly fixed to the retinal pigment epithelium 540, the stent 200, which has biodegradability, degrades. According to the above-described steps, retinal detachment can be treated.

As described above, the treatment method includes the introduction step S12 of introducing the transparent stent 200 into the vitreous body 510 of the eyeball 500, the expansion step S14 of causing the stent 200 to expansively deform inside the vitreous body 510 to bring the retina 530 into contact with the retinal pigment epithelium 540, and the placement step S15 of placing the stent 200 in the vitreous body 510 with the stent 200 keeping the retina 530 in contact with the retinal pigment epithelium 540. According to this treatment method, since the stent 200 is composed of a plurality of linear objects 200a, the stent 200 is able to bring the retina 530 into contact with the retinal pigment epithelium 540 with a contact area with the inner peripheral surface of the retina 530 reduced as compared with a balloon that presses the entire inner peripheral surface of the retina 530 during treatment, thus tightly fixing the retina 530 to the retinal pigment epithelium 540. Accordingly, retinal detachment can be treated without an increase in intraocular pressure. Furthermore, since the stent 200 has transparency, the stent 200 is unlikely to hinder vision even in the state of being placed in the vitreous body 510.

Furthermore, in the case of a conventional procedure that irradiates the retina 530 with a laser to bake and solidify the retina 530 and tightly fixes the retina 530 to the retinal pigment epithelium 540, a scar is left in the eyeball 500. In contrast to this, in the treatment method described above, which is a method of treating retinal detachment by placing the stent 200 in the vitreous body 510, a treatment can be performed without leaving any scar in the eyeball 500.

Moreover, in the case of a conventional procedure that removes a vitreous body 510 clouded by bleeding and fills the inside of the eyeball 500 with a gas to tightly fix the retina 530 to the retinal pigment epithelium 540, since a patient needs to stay in a hospital for about one week after surgery while lying face-down, the patient may feel distress. In contrast to this, in the treatment method presented herein, since the patient does not need to lie face-down after surgery, the hospital stay can be shortened and a burden on the patient can be reduced.

Additionally, while retinal detachment disease tends to recur due to an impact on the eyeball 500, since the stent 200 is placed in the vitreous body 510, the tightly-fixing force of the retina 530 against the retinal pigment epithelium 540 is reinforced, so that the patient can be allowed to play various sports.

Moreover, the treatment method further includes, ahead of the introduction step S12, the allocation step S11 of inserting the catheter 300 into the vitreous body 510 and allocating a delivery route leading to inside the vitreous body 510, and, in the introduction step S12, introduces the stent 200 into the vitreous body 510 via the delivery route. According to this treatment method, since the stent 200 can be introduced into the vitreous body 510 through the delivery lumen 302 of the catheter 300, the stent 200 can be more reliably introduced into the vitreous body 510.

Furthermore, the stent 200 is of a self-expandable type, and, in the introduction step S14, the stent 200 expands by itself. According to this treatment method, since means for expanding the stent 200 does not need to be provided, the configuration of the stent delivery system 10 can be simplified. Additionally, since no procedure for expanding the stent 200 is required, a more convenient procedure can be provided.

Moreover, in the introduction step S12, the stent delivery system 10, which includes the stent 200, the inner tube 20, on the outer periphery of which the stent 200 is arranged, and the outer tube 30 including the accommodation lumen 31, in which the inner tube 20 and the stent 200 are accommodated, and provided to be movable with respect to the inner tube 20, is introduced into the vitreous body 510, and, in the expansion step S14, an operation for extracting the outer tube 30 from the inner tube 20 discharges the stent 200 from between the inner tube 20 and the outer tube 30 to cause the stent 200 to expansively deform. According to this treatment method, the stent 200 can be more reliably caused to expansively deform inside the vitreous body 510.

Additionally, the stent 200 is made from a biodegradable material, and the stent 200 degrades in the vitreous body 510 after the placement step S15. According to this treatment method, since the stent 200 disappears from within the vitreous body 510 after the retina 530 is tightly fixed to the retinal pigment epithelium 540, there are beneficial effects in terms of safety in a long-term placement or a burden on the eyeball.

Moreover, the treatment method further includes, between the introduction step S12 and the placement step S15, the supply step S13 of supplying the medicine f, which promotes tight fixing of the retina 530 to the retinal pigment epithelium 540, to between the retina 530 and the retinal pigment epithelium 540. Therefore, the detached retina 530 can be efficiently tightly-fixed to the retinal pigment epithelium 540, so that the duration of treatment can be shortened.

Furthermore, as mentioned above, the stent 200 has transparency and is configured to be placed in the vitreous body 510 of the eyeball 500 in a state of expansively deforming inside the vitreous body 510 to keep the retina 530 in contact with the retinal pigment epithelium 540. According to the stent 200, since the stent 200 is composed of a plurality of linear objects 200a, the stent 200 is able to bring the retina 530 into contact with the retinal pigment epithelium 540 with a contact area with the inner peripheral surface of the retina 530 reduced as compared with a balloon that presses the entire inner peripheral surface of the retina 530 during treatment, thus tightly fixing the retina 530 to the retinal pigment epithelium 540. Accordingly, retinal detachment can be treated with an increase in intraocular pressure prevented. Additionally, since the stent 200 has transparency, the stent 200 is unlikely to hinder vision even in the state of being placed in the vitreous body 510.

Furthermore, the stent 200 is of a self-expandable type. According to the stent 200, since means for expanding the stent 200 does not need to be provided, the configuration of the stent delivery system 10 can be simplified. Additionally, since no procedure for expanding the stent 200 is required, a more convenient procedure can be provided.

Moreover, the stent 200 is made from a biodegradable material. According to the stent 200, since the stent 200 disappears from within the vitreous body 510 after the retina 530 is tightly fixed to the retinal pigment epithelium 540, there are beneficial effects in terms of safety in a long-term placement or a burden on the eyeball.

While the treatment method and the stent 200 according to the invention have been described above via an embodiment, the invention is not limited to only the treatment method and the stent 200 described in the above-mentioned embodiment, but can be altered or modified as appropriate based on claims.

For example, in the above-described embodiment, the stent 200 is of a self-expandable type. However, the stent can be of a balloon inflation type. The balloon inflation type stent can be a known conventional one. In a case where the stent is of a balloon inflation type, in the expansion step S14, spherically inflating the balloon causes the stent to spherically expand. Then, after the stent spherically expands, the balloon is immediately deflated. The above-mentioned operation enables the stent to bring the retina 530 into contact with the retinal pigment epithelium 540, thus tightly fixing the retina 530 to the retinal pigment epithelium 540. In a case where the balloon inflation type stent is used, since inflating the balloon is performed only when causing the stent to expand, retinal detachment can be treated while an increase in intraocular pressure is prevented as with the self-expandable type stent 200.

Furthermore, in the above-described embodiment, after the pars plana 550 is incised using a treatment tool, the catheter 300 is inserted into the vitreous body 510 through the incised portion. However, in a case where the distal end of the catheter 300 has a needle shape available for puncture, the pars plana 550 can be punctured directly with the catheter 300 to insert the catheter 300 into the vitreous body 510.

Moreover, the treatment device for use in the treatment method only needs to include at least a configuration capable of placing the stent 200 in the vitreous body 510, and such a configuration is not limited to the configurations described above with reference to the drawings. For example, imaging means (for example, an endoscope) can be used instead of the catheter 300, and the stent 200 can be introduced into the vitreous body 510 via, for example, a working channel of the imaging means.

Additionally, in the above-described embodiment, the stent 200 has biodegradability. However, the stent 200 does not need to have biodegradability as long as it is made from a material having transparency, and, thus can be made from, for example, acrylic resin (PMMA) or polycarbonate (PC).

Furthermore, in the above-described embodiments, extracting the outer tube 30 from the inner tube 20 exposes the gap portion 40 to the outside and causes the stent 200 to expand. However, extruding the inner tube 20 with respect to the outer tube 30 can expose the gap portion 40 to the outside and cause the stent 200 to expand.

Moreover, in the above-described embodiments, the expansion step S14 is performed after the supply step S13. However, the supply step can be performed after the expansion step is performed. More specifically, a drug-eluting stent (DES) on the outside surface of which the medicine f is coated is caused to expansively deform inside the vitreous body 510, thus bring the retina 530 into contact with the retinal pigment epithelium 540 (expansion step). After that, the medicine f is eluted from the outside surface of the stent and is then supplied to between the retina 530 and the retinal pigment epithelium 540 (supply step). As a result of this process, in the placement step S15, the tight fixing of the retina 530 to the retinal pigment epithelium. 540 is promoted.

Figure 10A:
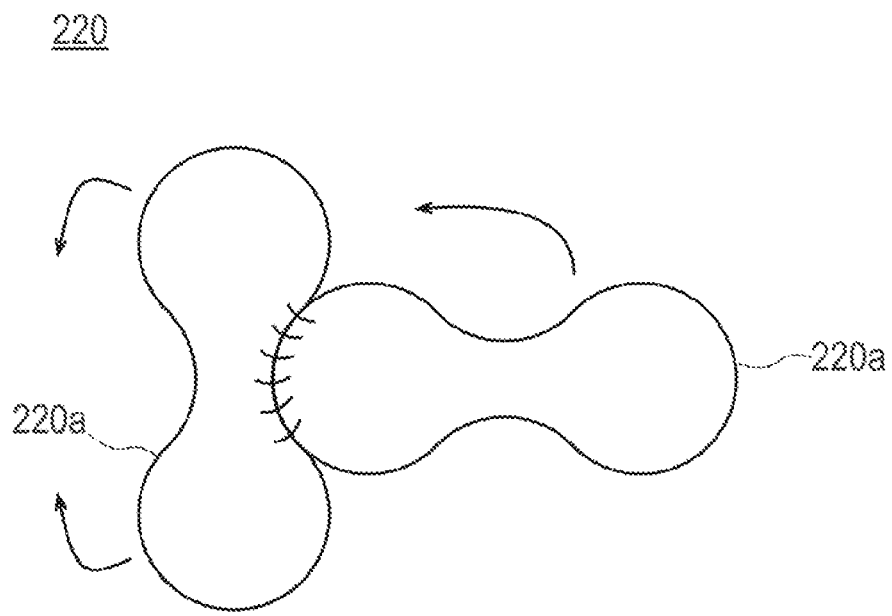
FIGS. 10A and 10B are diagrams illustrating a modification example of a stent in a state before expansively deforming and in a state after expansively deforming, respectively.
Figure 10B:
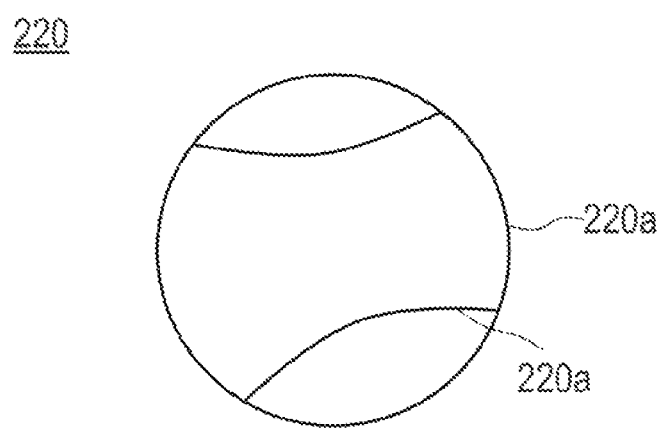
Figure 11:
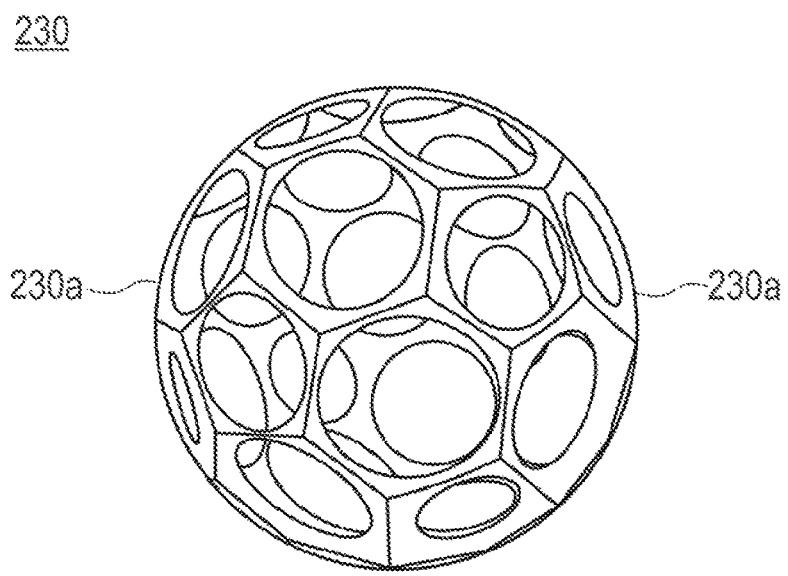
FIG. 11 is a diagram illustrating a modification example of a stent in a state after expansively deforming.

Additionally, in the above-described embodiments, as illustrated in FIG. 7, the stent 200 is configured to have a mesh-like shape in the expanded state. However, the stent 200 is not limited in shape as long as it is configured to have a spherical shape when expansively deforming, and can be configured, for example, as illustrated in FIG. 9 to FIG. 11.

Figure 9:
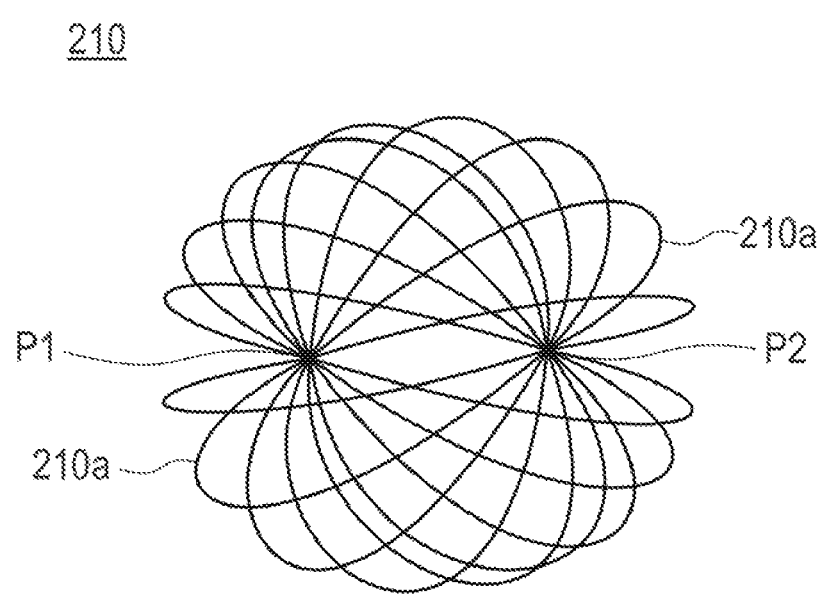
FIG. 9 is a diagram illustrating a modification example of a stent in a state after expansively deforming.

A stent 210 illustrated in FIG. 9 is composed of a plurality of linear objects 210a. The linear objects 210a are fixed to each other at two points P1 and P2, and are arranged in line contact with respective different positions on the inner peripheral surface of the retina. Additionally, a stent 220 illustrated in FIGS. 10A and 10B is composed of two dumbbell-like linear objects 220a. The two linear objects 220a deform in directions indicated by arrows illustrated in FIG. 10A and become a spherical shape such as that illustrated in FIG. 10B. Moreover, a stent 230 illustrated in FIG. 11 is composed of a plurality of linear objects 230a.

Figure 12:
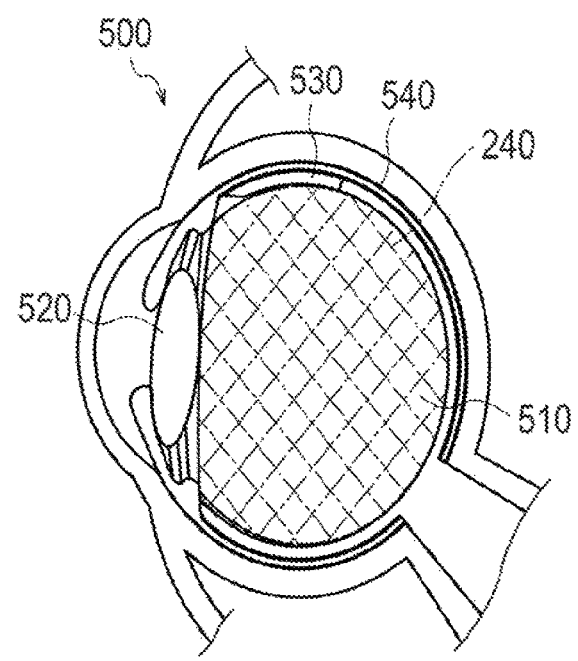
FIG. 12 is a diagram illustrating the behavior of varying an eyeball according to the shape of a stent being expanded.

Furthermore, as illustrated in FIG. 12, in the placement step S15, a stent 240 can be configured to deform the eyeball 500 in a vertically long shape according to the shape of the stent 240 in the expanded state, thus changing the focal length of the patient. This enables improving the vision of the patient.

DESCRIPTION OF REFERENCE NUMERALS AND SIGNS 10 stent delivery system,
20 inner tube,
30 outer tube,
30a gap,
31 accommodation lumen,
200, 210, 220, 230, 240 stent,
300 catheter,
302 delivery lumen, 500 eyeball,
510 vitreous body,
530 retina,
540 retinal pigment epithelium,
S11 allocation step,
S12 introduction step,
S13 supply step,
S14 expansion step,
S15 placement step.

What is claimed is:

1. A treatment method comprising:
   introducing a transparent stent into a vitreous body of an eyeball;
   discharging the stent from a stent delivery system, wherein discharging the stent releases the stent from the stent delivery system causing the stent to self-expand from a compressed state and deform into an expanded state having a substantially spherical shape inside the vitreous body to bring a retina of the eyeball into contact with a retinal pigment epithelium of the eyeball; and
   placing the stent in the vitreous body in the expanded state with the stent keeping the retina in contact with the retinal pigment epithelium;
   wherein the stent comprises a first linear object interconnected to a second linear object at a first connection region, wherein each of the first and second linear objects include a middle section and two end sections disposed opposite one another about the middle section, and wherein the first connection region includes a portion of the middle section of the first linear object and an end of the two end sections of the second linear object.

2. The treatment method according to claim 1, further comprising, ahead of introducing, inserting a catheter into the vitreous body and allocating a delivery route leading to inside the vitreous body, wherein, in the introducing, the stent is introduced into the vitreous body via the delivery route.

3. The treatment method according to claim 2, wherein the first and second linear objects each have a dumbbell-like shape, and wherein, in the expanded state, the first and second linear objects are deformed in a direction about each middle section forming the substantially spherical shape.

4. The treatment method according to claim 3, wherein, in the introducing, the stent delivery system, which includes the stent, an inner tube, on an outer periphery of which the stent is arranged, and an outer tube including an accommodation lumen, in which the inner tube and the stent are accommodated, and provided to be relatively movable with respect to the inner tube, is introduced into the vitreous body, and in the expanding, an operation for extracting the outer tube from the inner tube discharges the stent from between the inner tube and the outer tube to cause the stent to expansively deform to an approximate shape of the vitreous body.

5. The treatment method according to claim 4, wherein the stent is made from a biodegradable material, and the stent degrades in the vitreous body after the placement step.

6. The treatment method according to claim 5, further comprising, between the introducing and placing, supplying a medicine, which promotes tight fixing of the retina to the retinal pigment epithelium, to between the retina and the retinal pigment epithelium.

7. The treatment method according to claim 6, wherein, in placing, the eyeball is deformed according to a shape of the stent in the expanded state, so as to change a focal length of a patient.

8. A stent comprising:
   a transparent material configured to be placed in a vitreous body of an eyeball, wherein upon placing the stent into the vitreous body of the eyeball the transparent material is configured to expansively deform inside the vitreous body and keep a retina of the eyeball in contact with a retinal pigment epithelium of the eyeball,
   wherein the stent comprises a first linear object interconnected to a second linear object at a first connection region, wherein each of the first and second linear objects include a middle section and two end sections disposed opposite one another about the middle section, and wherein the first connection region includes a portion of the middle section of the first linear object and an end of the two end sections of the second linear object.

9. The stent according to claim 8, wherein the transparent material is of a self-expandable type.

10. The stent according to claim 9, wherein the stent is made from a biodegradable material.

11. The stent according to claim 10, wherein the stent is configured to deform the eyeball according to a shape of the stent in an expanded state, so as to change a focal length of the eyeball of a patient.

12. A treatment device comprising:
    a catheter; and
    a stent delivery system connected to the catheter, wherein the stent delivery system is configured to deliver a stent into a vitreous body of an eyeball, wherein the stent comprises:
    a transparent material configured to be placed in the vitreous body of the eyeball, wherein upon placing the stent into the vitreous body of the eyeball the transparent material is configured to expansively deform inside the vitreous body and keep a retina of the eyeball in contact with a retinal pigment epithelium of the eyeball,
    wherein the stent comprises a first linear object interconnected to a second linear object at a first connection region, wherein each of the first and second linear objects include a middle section and two end sections disposed opposite one another about the middle section, and wherein the first connection region includes a portion of the middle section of the first linear object and an end of the two end sections of the second linear object.

13. The treatment device according to claim 12, wherein the catheter comprises:
    a shaft extending in an axial direction along the catheter; and
    a hub formed at a proximal side of the shaft.

14. The treatment device according to claim 13, wherein a lumen is formed inside the shaft to deliver the stent to the vitreous body.

15. The treatment device according to claim 14, wherein a port in the hub connects with a distal end of the stent delivery device.

16. The treatment device according to claim 14, wherein the stent delivery device comprises:
    an inner tube formed along an axial direction of the stent delivery device;

an outer tube arranged to cover a distal portion side if the inner tube, wherein the stent is arranged between a distal portion of the inner tube and the distal side portion of the outer tube.

17. The treatment device according to claim 14, wherein the stent is configured to be discharged from the distal portion of the outer tube into the vitreous body.

18. The treatment device according to claim 14, wherein the stent delivery device further comprises a hand operation portion connected to the inner tube, wherein a force applied to the hand operation portion causes the inner tube to discharge the stent.

19. The treatment device according to claim 14, wherein the outer tube further includes a lumen, which is connected to a branch tube, wherein the lumen is configured to receive a medicine injected into the branch tube, and wherein the branch tube and the lumen are configured to convey the medicine to the vitreous body.

20. The treatment device according to claim 14, wherein the catheter of the treatment device is configured to be introduced into the vitreous body via an incision made in the eyeball.

* * * * *